United States Patent
Hermann

(10) Patent No.: US 10,925,928 B2
(45) Date of Patent: *Feb. 23, 2021

(54) METHOD FOR TREATING CHEMOTHERAPY-INDUCED MALE INFERTILITY

(71) Applicant: THE BOARD OF REGENTS OF THE UNIVERSITY OF TEXAS SYSTEM, Austin, TX (US)

(72) Inventor: Brian P. Hermann, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/367,383

(22) Filed: Dec. 2, 2016

(65) Prior Publication Data

US 2017/0119850 A1  May 4, 2017

Related U.S. Application Data

(63) Continuation of application No. 14/177,103, filed on Feb. 10, 2014, now Pat. No. 9,533,025.

(60) Provisional application No. 61/763,276, filed on Feb. 11, 2013.

(51) Int. Cl.
| | |
|---|---|
| *A61K 38/19* | (2006.01) |
| *A61K 31/255* | (2006.01) |
| *A61K 45/06* | (2006.01) |
| *A61K 38/18* | (2006.01) |
| *A61K 38/09* | (2006.01) |
| *A61K 9/00* | (2006.01) |

(52) U.S. Cl.
CPC .......... *A61K 38/193* (2013.01); *A61K 31/255* (2013.01); *A61K 45/06* (2013.01); *A61K 9/0019* (2013.01); *A61K 38/09* (2013.01); *A61K 38/185* (2013.01); *A61K 38/1825* (2013.01)

(58) Field of Classification Search
None
See application file for complete search history.

(56) References Cited

U.S. PATENT DOCUMENTS 5,817,453 A * 10/1998 Brinster ............. A01K 67/0275 435/1.1

OTHER PUBLICATIONS

Kotzur et al.,Reproductive Biology and Endocrinology (2017) 15:7, DOI 10.1186/s12958-016-0226-1.*
Benevides-Garcia, et al., Fertility and Sterility. 103(1:270-280, 2015.
De Lima, et al., Blood. 104(3):857-64, 2004.
Kim, et al., "Protection of spermatogenesis against gamma ray-induced damage by granulocyte colony-stimulating factor in mice." Andrologia. 43(2):87-93, 2011.
Mitchell, et al., "Male fertility and strategies for fertility preservation following childhood cancer treatment" In Wallace WHB, Kelnar CJH (eds); Endocrinopathy after Childhood Cancer Treatment. Endocr. Dev. Basel, Karger, vol. 15, 101-134, 2009.
Riikonen, et al., Stem Cells. 13:289-294, 1995.
Shetty, et al., "Regenerative potential of spermatogenesis after gonadotoxic therapies" In KE Orwig and BP Hermann (eds), Male Germline Stem Cells: Developmental and Regenerative Potential, Stem Cell Biology and Regenerative Medicine, Springer Science+ Business Media LLC, 2011.
Skaznik-Wikiel, et al., Fertil Steril. 99(7):2045-2054, 2013.
Willis, et al., Bone Marrow Transplantation. 43:97-934, 2009.
Zohni, et al., Human Reproductive. Pages 1-10, 2011, doi: 10.1093/humrep/der357.

* cited by examiner

*Primary Examiner* — Marianne P Allen
(74) *Attorney, Agent, or Firm* — Norton Rose Fulbright US LLP

(57) ABSTRACT

A method of ameliorating, inhibiting, preventing, or reducing male infertility in a subject undergoing or in need of chemotherapy by administering to the subject a granulocyte colony-stimulating factor in a protective amount, prior to, during or after administration of one or more chemotherapeutic agents to the subject.

3 Claims, 12 Drawing Sheets

A

B

METHOD FOR TREATING CHEMOTHERAPY-INDUCED MALE INFERTILITY

CONTINUING DATA

The present application is a continuation from U.S. application Ser. No. 14/177,103 filed Feb. 14, 2014, which claims priority to U.S. Provisional Application 61/763,276 filed Feb. 11, 2013.

STATEMENT REGARDING FEDERALLY FUNDED RESEARCH

This invention was made with government support under R00HD062687 and P30GM092334 awarded by the National Institutes of Health. The government has certain rights in the invention.

STATEMENT REGARDING PRIORITY

This Application claims priority to U.S. Provisional Patent Application No. 61/763,276 filed Feb. 11, 2013, which is incorporated herein by reference in its entirety.

BACKGROUND

Certain embodiments relate generally to the field of medicine. More particularly, certain embodiments concern compositions and methods for ameliorating chemotherapy-induced infertility.

Spermatogonial stem cells (SSCs) are adult stem cells found in the mammalian testis that are responsible for maintaining spermatogenesis throughout adult life. Spermatogenesis is a highly productive process, producing millions of sperm each day (1000 sperm/heart beat). Because of this high degree of proliferation, spermatogenesis is susceptible to chemotherapy treatments, which can lead to long-term or permanent infertility or reduced fertility. SSCs themselves do not divide frequently, but high doses of various chemotherapeutic agents have been shown to kill SSCs, the loss of which would result in permanent loss of spermatogenesis and male infertility.

Adult males who will undergo potentially-sterilizing chemotherapy can prospectively cryopreserve sperm from a semen sample for later use in the fertility clinic via in vitro fertilization (IVF) or intracytoplasmic sperm injection (ICSI). However, prepubertal boys who are not yet producing mature gametes cannot take advantage of this standard-of-care option for preserving their future fertility. This is a significant problem because the overall event-free survival rate for childhood cancers is approaching 80%, which enables patients to look beyond cancer to a productive life after cure. Moreover, parenthood is important to cancer survivors and distress over infertility can have long-term psychological and relationship implications.

To address this clinical need, several experimental technologies are on the horizon that may facilitate preserving the future fertility of prepubertal boys. Spermatogonial stem cell (SSC) transplantation is one experimental approach that may have application for preserving and restoring fertility of prepubertal boys. With this technology, SSCs would be harvested from the patient surgically prior to chemotherapy, cryopreserved, and stored until their reintroduction into the patient's testis sometime after chemotherapy treatment. This approach has the potential to regenerate spermatogenesis in these patients who currently have no other option to preserve their future fertility. Feasibility of this approach is supported by results in animal models including rodents, pigs, goats, bulls, dogs, and monkeys.

However, transplantation of cryopreserved testis cells isolated from patients with cancer carries an inherent risk of reintroducing contaminating malignant cells back into patients. Using rodent models, there are conflicting reports about the feasibility of separating SSCs from malignant cells using immune-based approaches and the current data for eliminating cancer cells from contaminated primate and human testicular cell suspensions is contradictory. Moreover, another major limiting factor to successful application of SSC transplantation in the clinic is that the number of SSCs which can be prospectively isolated from patients before treatment is lower than the number needed for successful SSC transplantation at a later date. Thus, while spermatogonial stem cell transplantation has proven effective for regenerating spermatogenesis and fertility in small and large animal models, clinical translation will likely lag until methods are developed to eliminate the risk of re-introducing malignant cells into a cancer survivor and isolate or amplify sufficient SSCs for transplant.

Testicular tissue xenografting is an alternative technique that may provide a therapeutic option for prepubertal cancer patients and avoids the risk of malignant cell contamination. Using this approach, intact testicular tissue grafts from immature mice, rats, hamsters, pigs, goats, and nonhuman primates were competent to produce complete spermatogenesis following ectopic transplantation under the skin of mouse hosts. Sperm retrieved from rodent grafts (freshly transplanted or cryopreserved) could be used for intracytoplasmic sperm injection (ICSI) to produce offspring. However, to date, there has only been one report of sperm production in grafts of cryopreserved prepubertal rhesus macaque testicular tissue from among numerous studies using monkey and primate tissue. Moreover, little is known about the risk of zoonotic disease transmission from germ cells derived from tissue transplanted in a xeno intermediate. Alternatively, grafts could be implanted back into the patients in the homotopic site (within the testis) or at a heterotopic site such as beneath the skin, but this approach bears the same risk of malignant cell contamination as SSC transplantation. Alternate strategies involving gamete production in vitro from cultured cells or tissue may provide options for fertility restoration for some patients, but their utility/efficacy have yet to be proven.

Yet another alternative approach would be to prospectively preserve SSCs from the toxicity of chemotherapy in their native testicular environment. Along those lines, several studies have investigated the use of hormone treatments to suppress the gonadotropins (i.e., FSH and LH). This approach reduces intratesticular testosterone levels, which protects testicular somatic cells and enhances the recovery of spermatogenesis from surviving SSCs. Prompted by these promising observations in lab animals, seven clinical trials tested this approach in adult humans, all but one study failed to demonstrate an improvement in sperm counts after gonadotropin suppression. Subsequently, gonadotropin suppression has received little attention as an option for male fertility preservation.

One previous study in mice from Kim and colleagues (Andrologia (2010) 43:87-93) reported similar protection of spermatogenesis in irradiated mice using granulocyte colony stimulating factor (G-CSF). In that study, mice were treated with G-CSF (100 µg/kg/day) for 3 days prior to 5 Gy of testicular gamma irradiation and the effects on spermatogenesis were measured 3 weeks later. The results demonstrate G-CSF treatment induced a modest improvement in the numbers of surviving differentiated spermatogonia following sub-sterilizing irradiation. While radiation and alkylating chemotherapy treatment are both used to kill malignant cells because they both target rapidly dividing cells, they have different mechanisms of action and their effects on spermatogenesis are different. By extension, methods used to protect spermatogenesis do not always have the same beneficial effects for radiation and chemotherapy insults. Indeed, other previous studies examining the use of gonadotropin suppression to protect spermatogenesis from cytotoxic insult demonstrated that beneficial effects in irradiated animals do not translate to chemotherapy. Specifically, rats treated with GnRH antagonists prior to sterilizing irradiation showed improved spermatogenic regeneration, while similar treatments prior to busulfan chemotherapy failed to promote spermatogenic regeneration. Thus, the prior results with irradiation cannot be extrapolated to nor are they predicative of G-CSF amelioration of chemotherapy-induced infertility.

Of note, the radiation dose employed in the prior art (5Gy irradiation+G-CSF) is considered sub-sterilizing, and thus, spontaneous cell survival is expected, particularly among the differentiated spermatogonia. Moreover, the time to analysis after G-CSF treatment and irradiation (21 days) measures effects at the level of differentiated Type-B spermatogonia, not stem cells. Specifically, the duration of spermatogenesis in mouse is 40.5 days (the amount of time required for a differentiating division of an a single spermatogonial stem cell to produce spermatozoa in the testis, and thus, assessment of stem cell survival or repopulation requires a longer time-frame for analysis. Indeed, bona fide assessment of spermatogenic regeneration from stem cells requires observation of complete spermatogenesis, which can only be appropriately evaluated at ~2 months following treatment to give sufficient time to allow exit of damaged spermatogonia from the testis and allow progeny from stem cells to differentiate beyond the latest stages of mitotic spermatogonia (i.e., prior to meiotic entry and spermiogenesis in haploid spermatids).

SUMMARY

Certain embodiments are directed to methods and compositions for maintaining and/or promoting fertility in a subject that will be, has been, or is being administered chemotherapy. Thus, the methods described herein can be used to ameliorate (lessen or render less severe) chemotherapy-induced infertility. In certain aspects the methods provided herein can maintain a sperm count over about 15 million sperm per milliliter and/or maintain motility and morphology sufficient for fertility. In certain aspects maintenance of fertility can include protection of spermatogonial stem cells from chemotherapy-induced damage and/or stimulation or priming of SSCs for regeneration after chemotherapy, or a combination of these mechanisms. As used herein the term "protect," refers to decreasing the probability of an event, such as sterility. In the context of medicine, "protection" generally refers to an action taken to decrease the chance of getting a disease or condition, in this application the condition is chemotherapy-induced male infertility, which may include azoospermia (no sperm production), oligospermia (low sperm production), asthenozoospermia (poor/absent sperm motility), teratospermia (poor sperm morphology/shape), or combinations of these conditions of defective sperm count, motility, and morphology. Thus, protecting spermatogonial stem cells decreases the probability that the SSC will be killed, inactivated, or otherwise caused to be abnormal by chemotherapy resulting in the amelioration of chemotherapy-induced infertility. Furthermore, stimulation or priming of the regenerative capacity of SSCs can also contribute to the recovery of fertility after chemotherapy by counteracting any cellular mechanisms that result in the a decreased renewal or production of daughter cells.

Certain embodiments are directed to methods of ameliorating, inhibiting, preventing, or reducing chemotherapy-induced infertility in a subject undergoing chemotherapy. In certain aspects the methods comprise administering to the subject prior to, during, and/or after chemotherapy a granulocyte colony-stimulating factor (G-CSF) in an amount sufficient to maintain fertility in a subject. Infertility is typically defined in a subject by having one or more of ejaculated sperm count less than 15 million sperm per milliliter, sperm motility of less than 35%, and/or normal sperm morphology less than 10%. Fertility/infertility characteristic can be assessed by analysis of sperm sample by trained personnel. As used herein the terms "administration," "administering," or the like, when used in the context of providing a composition to a subject generally refers to providing to the subject one or more pharmaceutical compositions in combination with an appropriate delivery vehicle by any means such that the administered composition achieves one or more of the intended biological effects for which the composition was administered. By way of non-limiting example, a composition may be administered parenteral, subcutaneous, intravenous, intramuscular, intraperitoneal, transdermal, intratesticular, or buccal routes of delivery. In certain aspects granulocyte colony-stimulating factor (G-CSF) is administered to the subject prior to administration of one or more chemotherapeutic agents. In a further aspect granulocyte colony-stimulating factor is administered to the subject after administration of one or more chemotherapeutic agents. Granulocyte colony-stimulating factor may also be administered to the subject prior to administration of one or more chemotherapeutic agents and after administration of one or more chemotherapeutic agents. In certain aspects granulocyte colony-stimulating factor is administered to the subject prior to and/or following administration of one or more chemotherapeutic agents. In certain aspects a composition comprising G-CSF is administered 1, 2, 3, 4, 5, 6, 7, or more days or weeks prior to chemotherapy. In a further aspect the protective composition is administered concurrently with chemotherapy. In still a further aspect the protective compositions are administered 1, 2, 3, 4, 5, 6, 7, days or week after chemotherapy. G-CSF can be administered 1, 2, 3, 4, 5, 6, 7, or times before, during an/or after chemotherapy. In certain aspects granulocyte colony-stimulating factor may be administered at a dose of from about 0.1, 1, 10, 50, 100, 200 µg/kg/day to about 50, 100, 150, 200, 300, 500 µg/kg/day, including all values and ranges there between.

In certain embodiments the subject is a mammal. In a further aspect the mammal is a human, a sporting animal, livestock, or an endangered species. In certain aspects the subject is prepubertal.

The term "stem cell" refers to a cell having the capacity to self-renew and to differentiate. In the testis, spermatogonial stem cells have the capacity to self-renew and produce differentiating spermatogonia, which ultimately produce male gametes (spermatozoa).

By "stem cell generation" refers to any biological process that gives rise to stem cells. Such processes include the proliferation of existing stem cells, stem cell self-renewal, or de novo production of new stem cells from another cell.

The term "self renewal" as used herein refers to the process by which a stem cell divides (mitosis) to generate one (asymmetric division) or two (symmetric division) daughter cells with development potentials that are indistinguishable from those of the mother cell. Self-renewal involves both proliferation and the maintenance of an undifferentiated state.

By "subject" is meant a mammal, including, but not limited to, a human or non-human mammal, such as a bovine, equine, canine, ovine, or feline.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized).

The term "providing" is used according to its ordinary meaning "to supply or furnish for use." In some embodiments, the protein is provided directly by administering the protein. In other embodiments, a protein is effectively provided by administering a nucleic acid that encodes the protein. In certain aspects the invention contemplates compositions comprising various combinations of nucleic acid, antigens, peptides, and/or epitopes.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Furthermore, the word "may" is used throughout this application in a permissive sense (i.e., having the potential to, being able to), not in a mandatory sense (i.e., must).

The term "include," and derivations thereof, mean "including, but not limited to."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to demonstrate certain embodiments. The invention may be better understood by reference to one or more of these drawings in combination with the detailed description of the specification presented herein.

FIG. 1 illustrates the timing of experimental administration of G-CSF and busulfan alkyating chemotherapy in the context of a study testing spermatogonial stem cell transplantation. Male rhesus macaques were used as recipients for spermatogonial stem cell transplantation after busulfan treatment. In order to restore the hematopoietic system after busulfan chemotherapy, autologous transplants of hematopoietic stem cells harvested from the peripheral blood (PBSCs) following G-CSF mobilization were used. Animals received daily subcutaneous injections with the cytokine G-CSF (and in some cases, also SCF) for six days to mobilize hematopoietic stem cells from the bone marrow into the general circulation. PBSCs were collected on day 0 by apheresis using the indwelling central line for venous access. Twenty-four hours after completing apheresis, animals were treated with busulfan (labeled arrow). Approximately forty-two hours after completing apheresis (~18 hours after busulfan treatment), animals were transfused with autologous PBSCs collected by apheresis. Two days later, animals received one subcutaneous injection of neulasta (long-acting G-CSF) to stimulate rapid expansion of engrafted stem cells and hematopoietic recovery. Animals were monitored closely for hematopoietic deficits with weekly (or more frequent) complete blood count (CBC). Approximately 10-12 weeks after busulfan treatment, animals received SSC transplants (when sperm counts were 0 for two consecutive weeks). Weekly ejaculated sperm counts measured the effect of busulfan on spermatogenesis and the progression of spermatogenic recovery after transplant.

DESCRIPTION

Figure 1:
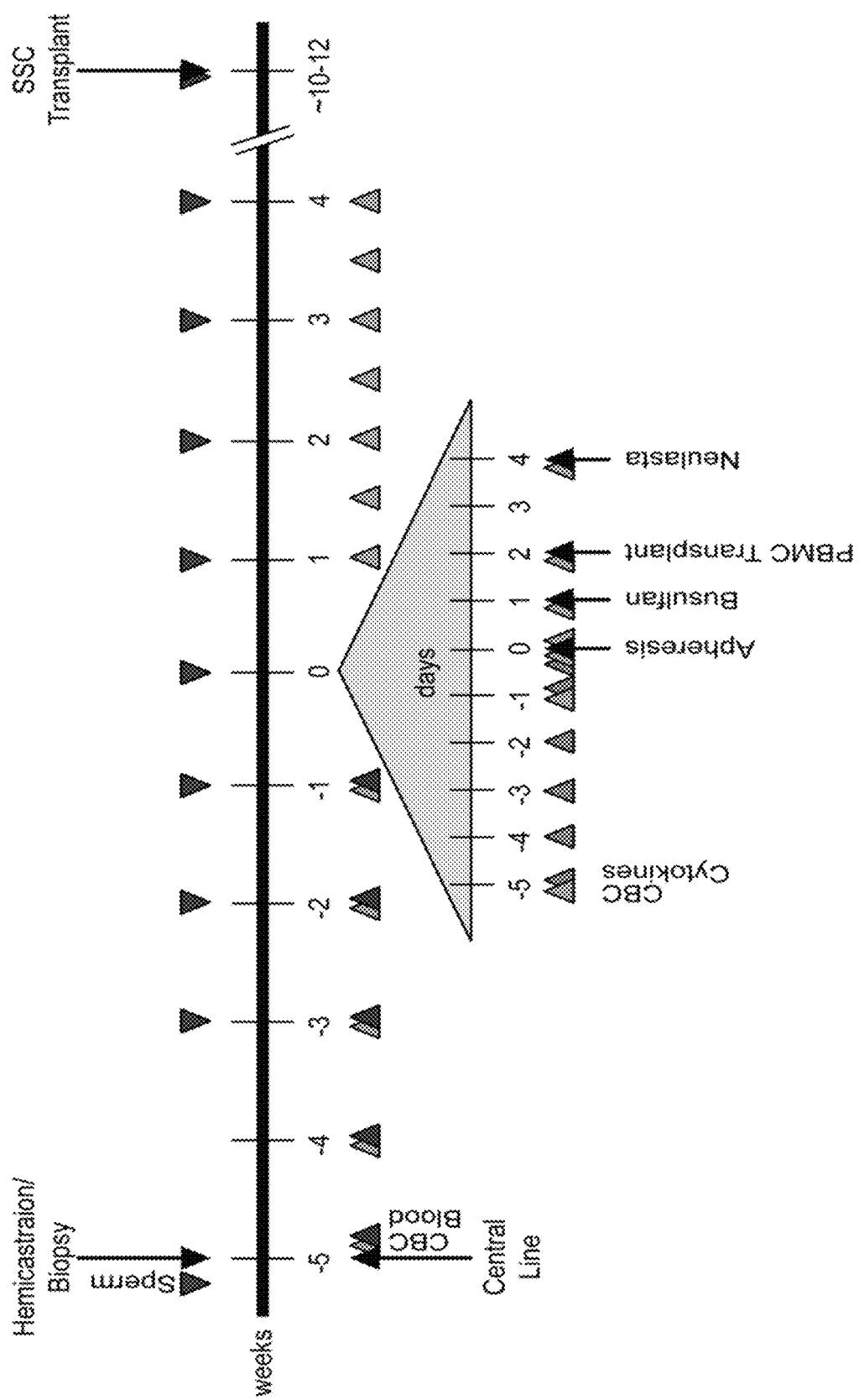
FIG. 1. Timeline for rhesus macaque granulocyte colony stimulating factor (G-CSF) and chemotherapy administration.

Male infertility is a long-term side effect of childhood cancer treatments. Preserving fertility in these patients has been a major research focus over the last decade. Experimental investigation of prepubertal male fertility preservation has mainly focused on invasive (surgical) testicular tissue retrieval, long-term cryogenic storage, and subsequent grafting/transplantation to produce gametes, all of which involve substantial risk and expense. The alternative strategy described herein involves prospective treatment to prevent male infertility and/or promote fertility restoration with a less expensive, FDA-approved drug. This could potentially obviate the need for invasive intervention, and thus, has the potential to significantly change clinical management of infertility after chemotherapy. Thus, G-CSF can be used as a simple and non-invasive agent to maintain and/or restore male fertility in patients receiving potentially sterilizing chemotherapy for cancer and other disorders (e.g., those requiring bone marrow transplant).

Spermatogonial stem cells (SSCs) maintain spermatogenesis in mammalian testes and are essential for male fertility. Spermatogenesis is the process by which spermatozoa are produced from spermatogonial stem cells through mitosis and meiosis. The initial cells in this pathway are spermatogonial stem cells, which produce differentiating spermatogonia and self-renewing SSCs. The differentiating spermatogonia yield primary spermatocytes by mitosis. Each primary spermatocyte divides meiotically to produce two secondary spermatocytes; each secondary spermatocyte then completes meiosis as it divides into two spermatids that develop into mature spermatozoa, also known as sperm cells, through the process of spermiogenesis. Thus, spermatogonial stem cells give rise to differentiating spermatogonia, which give rise to primary spermatocytes, which give rise to secondary spermatocytes, and the secondary spermatocytes divide to produce spermatids, which undergo morphological differentiation to spermatozoa. Spermatozoa are the mature male gametes in many sexually reproducing organisms. Thus, spermatogenesis is the male version of gametogenesis. In mammals, spermatogenesis occurs in testes (also known as testicles) and sperm subsequently gain full capacity for fertilization in the epididymides. Spermatogenesis is essential for sexual reproduction and starts at puberty and usually continues uninterrupted until death.

Loss of SSCs or loss of SSCs' capability to produce spermatogenesis due to chemotherapy treatment for cancer leads to male infertility in many cancer survivors. While strategies to treat infertility in these patients are in development (e.g., SSC transplantation) it may be possible to prospectively prevent or minimize infertility after cancer treatment, and by extension, obviate the need for invasive techniques like SSC harvesting by testicular biopsy.

Meta-analysis of published studies reporting sperm counts in rhesus macaques after busulfan chemotherapy was performed. The analysis indicated that spermatogenesis could be protected from the detrimental effects of busulfan chemotherapy by treatment with the cytokine granulocyte colony-stimulating factor (G-CSF). The term "granulocyte colony-stimulating factor" as used herein is defined as the protein produced from the gene encoding colony-stimulating factor 3 and is abbreviated as G-CSF and CSF3, and known by trade names neupogen, neulasta, filgrastim, etc. One example of human G-CSF can be found in GenBank accession number AAA35882.1, which is incorporated herein by reference as of the filing date of this application. A G-CSF can be used in any form, whether endogenous to the cells, produced exogenously, recombinant, or otherwise modified in any way.

G-CSF was used in one of the studies to mobilize hematopoietic stem cells (HSCs) into the general circulation prior to collection by apheresis for autologous HSC transplants to counteract busulfan-induced myelosuppression. Additional studies were conducted in a mouse model where 5 week-old mice were treated with G-CSF for one week and administered busulfan on day 3, mimicking the approach used to administer G-CSF in monkeys. G-CSF treatment in mice and monkeys led to significantly better recovery of spermatogenesis after busulfan treatment than controls, and likely restored their fertility. These results suggest G-CSF treatment protects SSCs, which express G-CSF receptor (CSF3R) mRNA and protein, from the gonadotoxic insult of chemotherapy, and/or promotes regeneration of spermatogenesis from surviving SSCs.

In certain aspects, but not to be limiting to any particular hypothesis, G-CSF prevents infertility after chemotherapy treatment by preventing loss of SSCs via apoptosis. These results also suggest that G-CSF treatment promotes spermatogenic regeneration from spermatogonial stem cells that survive the gonadotoxic insult of chemotherapy by acting through the G-CSF receptor protein. In certain aspects, but not to be limited by any particular hypothesis, G-CSF prevents infertility after chemotherapy treatment by promoting spermatogenic regeneration from surviving SSCs. Thus, the detrimental effects of chemotherapy that lead to male infertility can be ameliorated by treatment with the cytokine G-CSF.

In certain aspects G-CSF can be administered before chemotherapy; during chemotherapy; after chemotherapy; before and during chemotherapy; before and after chemotherapy; during and after chemotherapy; or before, during, and after chemotherapy. G-CSF can be delivered or administered via a number of routes, including subcutaneous, intraperitoneal, intravenous, or intratesticular administration. In certain aspects, G-CSF is delivered locally, e.g., through an intratesticular route, to patients having a cancer that may be responsive to G-CSF (e.g., leukemia) in which systemic G-CSF administration would be contraindicated. Moreover, G-CSF can be effective in both adults and prepubertal males treated with chemotherapy since SSCs are proliferating in both instances. Thus, G-CSF treatment is effective regardless of the developmental stage of testicles (e.g., pre-pubertal or adult).

Mechanistically, G-CSF treatments may provide protection from the detrimental effects of chemotherapy by protecting SSCs from apoptosis and also promoting spermatogenic regeneration. That is, pre-treatment with G-CSF before busulfan administration, can promote SSC survival by an anti-apoptotic mechanism. Post-treatment with G-CSF can promote quicker spermatogenic regeneration by inducing or stimulating proliferation of any unaffected SSCs after chemotherapy. Both mechanisms of G-CSF action may play complementary roles in promoting better spermatogenic recovery after chemotherapy.

G-CSF treatment may be combined with other treatments to provide for recovery of spermatogenesis after chemotherapy. Glial cell-lined derived neurotrophic factor (GDNF), which is secreted by somatic cells of the testis, is a growth factor that promotes SSC survival and self-renewal, in vitro, and is involved in spermatogenesis, in vivo. Further, addition of fibroblast growth factor 2 (FGF2 or bFGF) and colony-stimulating factor 1 (CSF1) has been shown to enhance mouse SSC self-renewal and augment stem cell expansion in vitro. Thus, co-treatment with G-CSF along with any combination of these or other growth factors (e.g., GDNF, FGF2/bFGF, CSF1 and the like) is contemplated to further augment recovery of spermatogenesis after chemotherapy.

Gonadotropin-releasing hormone (GnRH), also known as Luteinizing-hormone-releasing hormone (LHRH) and luliberin, is a trophic peptide hormone responsible for the release of follicle-stimulating hormone (FSH) and luteinizing hormone (LH). The peptide belongs to gonadotropin-releasing hormone family. GnRH activity is very low during childhood, and is activated at puberty or adolescence. During the reproductive years, pulse activity is critical for successful reproductive function as controlled by feedback loops. Elevated prolactin levels decrease GnRH activity. Certain embodiments are directed to methods that combine G-CSF treatment with gonadotropin suppression via GnRH agonist/antagonist treatment, which reduces intratesticular testosterone levels, to further mitigate damage of testicular somatic cells and enhance the recovery of spermatogenesis from surviving SSCs. Modifications of GnRH's structure has led to GnRH1 analog medications that either stimulate (GnRH1 agonists) or suppress (GnRH antagonists) the gonadotropins.

I. PHARMACEUTICAL FORMULATIONS AND ADMINISTRATION

Certain embodiments are directed to protective compositions that when administered to a subject about to have, is having, or has had chemotherapy preserve at least some capacity for spermatogenesis resulting in viable sperm. In certain aspects the subject is going to, is being administered, or has been administered chemotherapeutic compositions comprising 1, 2, 3 or more chemotherapeutic agents. The subject can be administered a composition comprising a G-CSF protein or active fragment thereof with one or more of the following: a pharmaceutically acceptable diluent, a carrier, a solubilizer, an emulsifier, and/or a preservative. Such compositions may contain an effective amount of at least one fertility maintenance agent. Thus, the use of one or more fertility maintenance agents that are provided herein in the preparation of a pharmaceutical composition of a medicament is also included. Such compositions can be used as supplemental treatments in the treatment of a variety of cancers or other conditions treated by administering chemotherapy. In certain aspects a subject is administered a protective amount of a composition. The term "effective amount" or "protective amount", as used herein describes an effective amount of a compound administered to a subject, simultaneously, separately, or sequentially with one or more chemotherapeutic agents, which is sufficient to reduce, prevent or otherwise ameliorate the adverse side effects of the chemotherapeutic drugs on the fertility of the subject and/or the reproductive system including the cells and tissue involved in spermatogenesis.

The protective agents may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form may depend upon the mode of administration and the particular disease being treated.

The term "chemotherapeutic agent" or "chemotherapy" as used herein is defined as a drug used as treatment for cancer and other disorders requiring their action. In certain aspects radiotherapy is specifically excluded. Chemotherapeutic agents include agents that directly cross-link DNA, agents that intercalate into DNA, and agents that lead to chromosomal and mitotic aberrations by affecting nucleic acid synthesis. Examples of chemotherapeutic agents include, but are not limited to: doxorubicin, daunorubicin, mitomycin, actinomycin D, bleomycin, cisplatin, etoposide, tumor necrosis factor, taxol, vincristine, vinblastine, carmustine, melphalan, cyclophosphamide, chlorambucil, busulfan, fluorouracil ("5FU") and lomustine. Any agent may be used alone, or in combination with other agents, after pre-treatment and/or post-treatment of the patient with granulocyte colony-stimulating factor. The pretreatment and/or post-treatment of the subject with a granulocyte colony-stimulating factor inhibits, prevents, or reduces infertility including adverse effects on spermatogonial stem cells and/or spermatogenesis in a subject during chemotherapeutic treatment for cancer or other non-malignant disorder in the subject without significantly inhibiting the efficacy of such agents. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. It is specifically contemplated that any of the compounds or derivatives or analogs, can be used with these combination therapies.

As used herein the terms "subject" generally refers to a mammal, and in particular to a human. In one embodiment, the subject who receives granulocyte colony-stimulating factor is one who is scheduled for or has already received chemotherapy. For example, the subject can be a human patient or an animal diagnosed with a cancer for which chemotherapy is considered to be an advantageous treatment. In certain aspects radiotherapy is specifically excluded as a therapy to be used in combination with G-CSF treatment.

The term "to treat" as used herein is defined as the practice of administering treatment for a medical condition or disease.

The terms "in need of treatment," "in need thereof," "who would benefit from such treatment," or the like when used in the context of a subject being administered a chemotherapy, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

As used herein the terms "reducing," "inhibiting" and "ameliorating," when used in the context of modulating a pathological or disease state, generally refers to the prevention and/or reduction of at least a portion of the negative consequences of the disease state or side-effects of the treatment for a disease state.

Acceptable formulation components for pharmaceutical preparations are nontoxic to recipients at the dosages and concentrations employed. In addition to the protective agents that are provided, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences,* 18 th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, intravenous, intraperitoneal, oral, subcutaneous administration, intraarterial, intramuscular, and by perfusion through a regional catheter. Local administration to the testes is also contemplated. When administering the compositions by injection, the administration may be by continuous infusion or by single or multiple boluses. For parenteral administration, the agents may be administered in a pyrogen-free, parenterally acceptable aqueous solution comprising the desired agent(s) in a pharmaceutically acceptable vehicle. A particularly suitable vehicle for parenteral injection is sterile distilled water in which one or more protective agents are formulated as a sterile, isotonic solution, properly preserved.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as sucrose, trehalose, or glycine, may be used. Typically, such stabilizers will be added in minor amounts ranging from, for example, about 0.1% to about 0.5% (w/v). Surfactant stabilizers, such as TWEEN®-20 or TWEEN®-80 (ICI Americas, Inc., Bridgewater, N.J., USA), may also be added in conventional amounts.

The components used to formulate the pharmaceutical compositions are preferably of high purity and are substantially free of potentially harmful contaminants (e.g., at least National Food (NF) grade, generally at least analytical grade, and more typically at least pharmaceutical grade). To the extent that a given compound must be synthesized prior to use, the resulting product is typically substantially free of any potentially toxic agents.

For the compounds of the present invention, alone or as part of a pharmaceutical composition, such doses are between about 0.0001 mg/kg and 1 mg/kg body weight, preferably between about 1 and 100 µg/kg body weight, most preferably between 1 and 10 µg/kg body weight.

Therapeutically effective doses will be easily determined by one of skill in the art and will depend on the severity and course of the disease, the patient's health and response to treatment, the patient's age, weight, height, sex, previous medical history and the judgment of the treating physician.

In certain aspects the subject may have a solid or blood borne tumor. In such cases, embodiments may further involve administering chemotherapy to the subject. Compositions may be administered to the subject before, after, or at the same time as chemotherapy. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 or more months.

In some embodiments, the cancer that is administered the composition(s) described herein may be a bladder, blood, bone, bone marrow, brain, breast, colorectal, esophagus, gastrointestine, head, kidney, liver, lung, nasopharynx, neck, pancreas, prostate, skin, stomach, testicular, or tongue cell. In certain aspects the cancer is leukemia, lymphoma, or neuroblastoma.

The term "pharmaceutically or pharmacologically acceptable" as used herein refers to molecular entities and compositions that do not produce adverse, allergic, or other untoward reactions when administered to an animal or a human.

The term "pharmaceutically acceptable carrier" as used herein includes any and all solvents, dispersion media, coatings, antibacterial and antifungal agents, isotonic and absorption delaying agents and the like.

As used herein, terms such as "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release," "controlled release," or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

II. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Rhesus macaques have been used to model long-term male infertility and cancer survivorship by using high-dose alkylating chemotherapy (busulfan) in which infertility was due to loss of SSCs. Subsequently, this model was used in a study to test whether SSC transplantation could be used to reverse the chemotherapy-induced male infertility. However, in order to maximize animal health after high-dose busulfan treatment, prospective, autologous hematopoietic stem cell (HSC) transplant was instituted to reconstitute the hematopoietic system. Clinically, HSC transplantation utilizes either bone marrow aspirates or stem cells isolated from the peripheral circulation by leukapheresis (i.e., so-called peripheral blood stem cells or PBSCs). To maximize the concentration of PBSCs in the general circulation prior to collection, patients typically undergo a 5-6 day mobilization regimen involving treatment with the cytokine G-CSF to stimulate the neutrophil lineage.

In the rhesus macaque study, G-CSF mobilization was used to provide sufficient autologous PBSCs for apheresis collection and transplant to reconstitute the hematopoietic system. FIG. 1 illustrates the relative timing of experimental procedures for macaques in that study, including autologous transplants of peripheral blood stem cells (PBSCs) used to restore the hematopoietic system after busulfan chemotherapy. Indwelling central venous catheters were placed in the right internal jugular vein at the time of testicular tissue harvesting or approximately 5 weeks before PBSC harvest via apheresis. Autologous blood was collected for 5 weeks (red triangles) and pooled to prime the apheresis tubing set.

Animals received daily subcutaneous injections with the cytokine G-CSF for 6 days to mobilize hematopoietic stem cells from the bone marrow into the general circulation. PBSCs were collected on day 0 by apheresis using the indwelling central line for venous access. Twenty-four hours after completing apheresis, animals were treated with busulfan (labeled arrow). Approximately 42 hours after completing apheresis (~18 hr after busulfan treatment), animals were transfused with autologous PBSCs collected by apheresis. Two days later, animals received one subcutaneous injection of Neulasta (a long-acting form of G-CSF) to stimulate rapid expansion of engrafted PBSCs and hematopoietic recovery. Animals were monitored closely for hematopoietic deficits with weekly (or more frequent) complete blood count (CBC). Approximately 10-12 weeks after busulfan treatment, animals received SSC transplants (when sperm counts were 0 for 2 consecutive weeks). Weekly ejaculated sperm counts measured the effect of busulfan on spermatogenesis and the progression of spermatogenic recovery after SSC transplant, which demonstrated successful regeneration of spermatogenesis in many animals, including the monkeys of this study.

Figure 2:
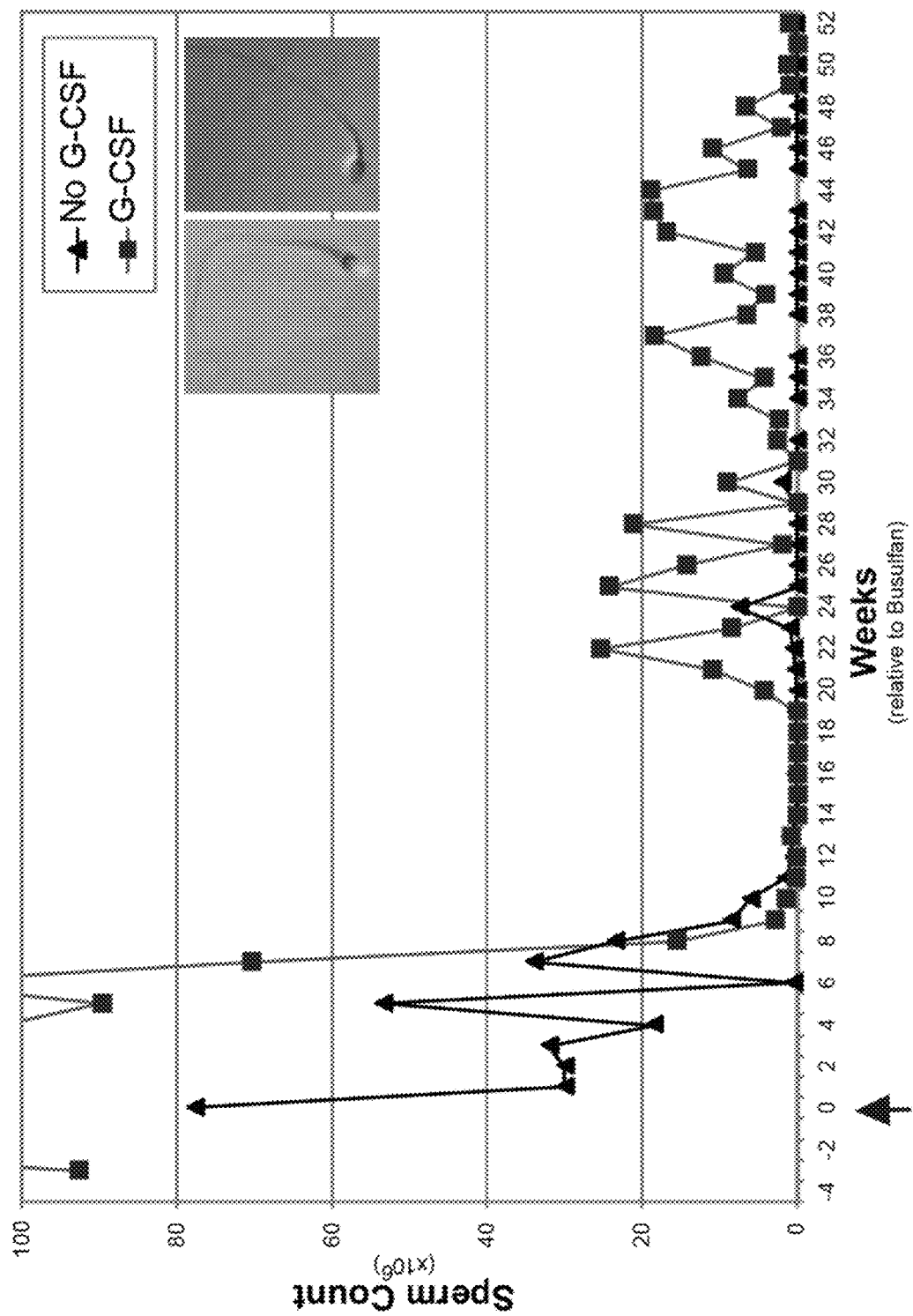
FIG. 2. G-CSF protects macaque spermatogenesis from busulfan chemotherapy. A meta-analysis of sperm counts (total sperm per ejaculate) are shown from animals treated with busulfan alone (triangles; no G-CSF) or G-CSF+PBSC transplants (squares; G-CSF). Sperm counts are means from 2 macaques for "no G-CSF" group and from 3 macaques in the "G-CSF" group. For all animals, busulfan was administered on week 0 (noted with arrow). The three animals receiving G-CSF and PBSC transplants were allogeneic SSC transplant recipients and did not exhibit any evidence of donor SSC engraftment, and thus, all sperm observed in ejaculates after busulfan treatment and SSC transplant was only from recovering endogenous spermatogenesis. Insets show representative rhesus sperm.

Subsequently, a meta-analysis of (1) the results of an initial study of busulfan effects on rhesus spermatogenesis and (2) results of a recent transplant study, revealed a surprising effect of G-CSF on the sensitivity of spermatogenesis to busulfan chemotherapy (FIG. 2). Comparison was between the mean sperm counts from (1) two animals which received 8-12 mg/kg busulfan without G-CSF (FIG. 2, triangles, no-G-CSF) and (2) three animals which received 8-11 mg/kg busulfan plus G-CSF mobilization and PBSC transplants (FIG. 2, squares, G-CSF). As reported previously, in the absence of G-CSF treatment, busulfan caused loss of spermatogenesis (azoospermia) for at least one year (FIG. 2, triangles). But, surprisingly, animals which were treated with G-CSF and received PBSC transplants recovered spermatogenesis as early as 20 weeks after busulfan treatment (FIG. 2, squares). The three animals receiving G-CSF and PBSC transplants were allogeneic SSC transplant recipients which never exhibited any evidence of donor SSC engraftment, and thus, all sperm observed in ejaculates after busulfan treatment or SSC transplant was only from recovering endogenous spermatogenesis. One of the monkeys included in the G-CSF group (FIG. 2, squares) received SCF in addition to G-CSF, but there was no apparent difference in spermatogenic recovery in this animal compared with the other two (data not shown). This meta-analysis suggested that G-CSF treatment and PBSC transplant protected spermatogenesis from busulfan-induced toxicity.

Since previous work demonstrated that hematopoietic stem cells transplanted into the testis cannot contribute to spermatogenesis, it was reasoned that recovery of spermatogenesis in macaques was due to G-CSF injections rather than intravenous PBSC transplants. It is unknown the extent to which G-CSF or its receptor (CSF3R) are involved in normal spermatogenesis in any species.

Example 2

Figures 3A, 3B, 3C, 3D:
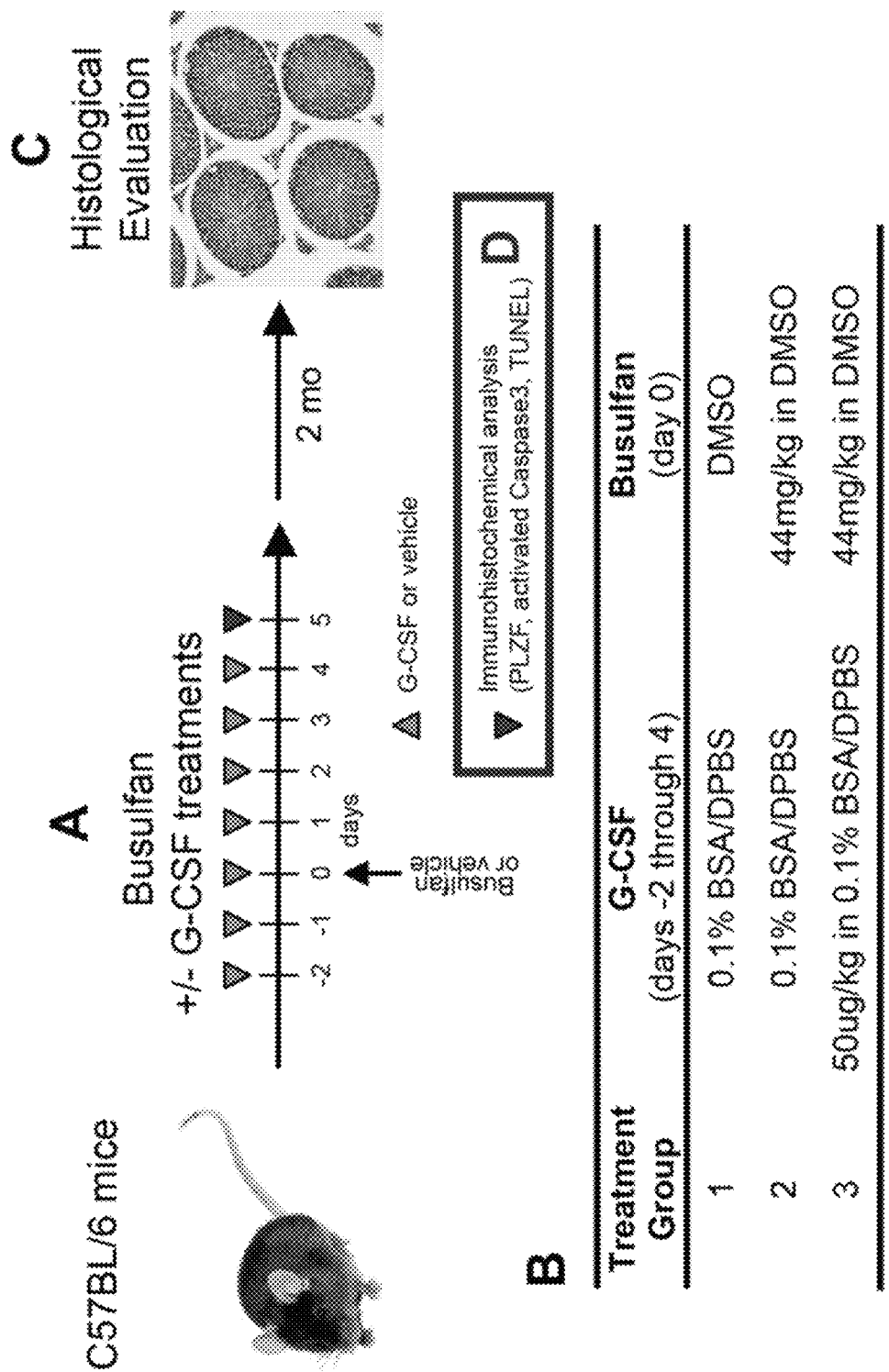
FIGS. 3A-3D. This study evaluated the chronic and acute effects of G-CSF treatment on susceptibility to cytotoxic damage by busulfan alkylating chemotherapy. (A) Five-week old C57BL/6 mice were treated with a sterilizing dose of busulfan (44 mg/kg) on day 0. Some busulfan-treated mice also received injections of recombinant human G-CSF (50 μg/kg/day) on days −2 through 4 (seven days total, see group 3 in B). (B) 3 animals were used for each of three treatment groups as shown. Animals in group 1 served as an "untreated" control group (received 0.1% BSA/DPBS and DMSO vehicles only), while those in group 2, which received only busulfan (plus 0.1% BSA/DPBS vehicle), served as positive controls for busulfan cytotoxicity. Animals in the experimental group 3 received both busulfan and daily G-CSF injections. (C) 8-10 weeks after treatment, some of the mice were euthanized and testes removed for histological evaluation of spermatogenesis. (D) In an "acute" study, testes were removed on day 5 of the experiment (one day after the last G-CSF treatment, dark triangle). These testis tissues were used for immunohistochemical analysis of undifferentiated spermatogonia (PLZF) and apoptosis (activated Caspase 3 and TUNEL, see FIGS. 10-12).
Figure 4:
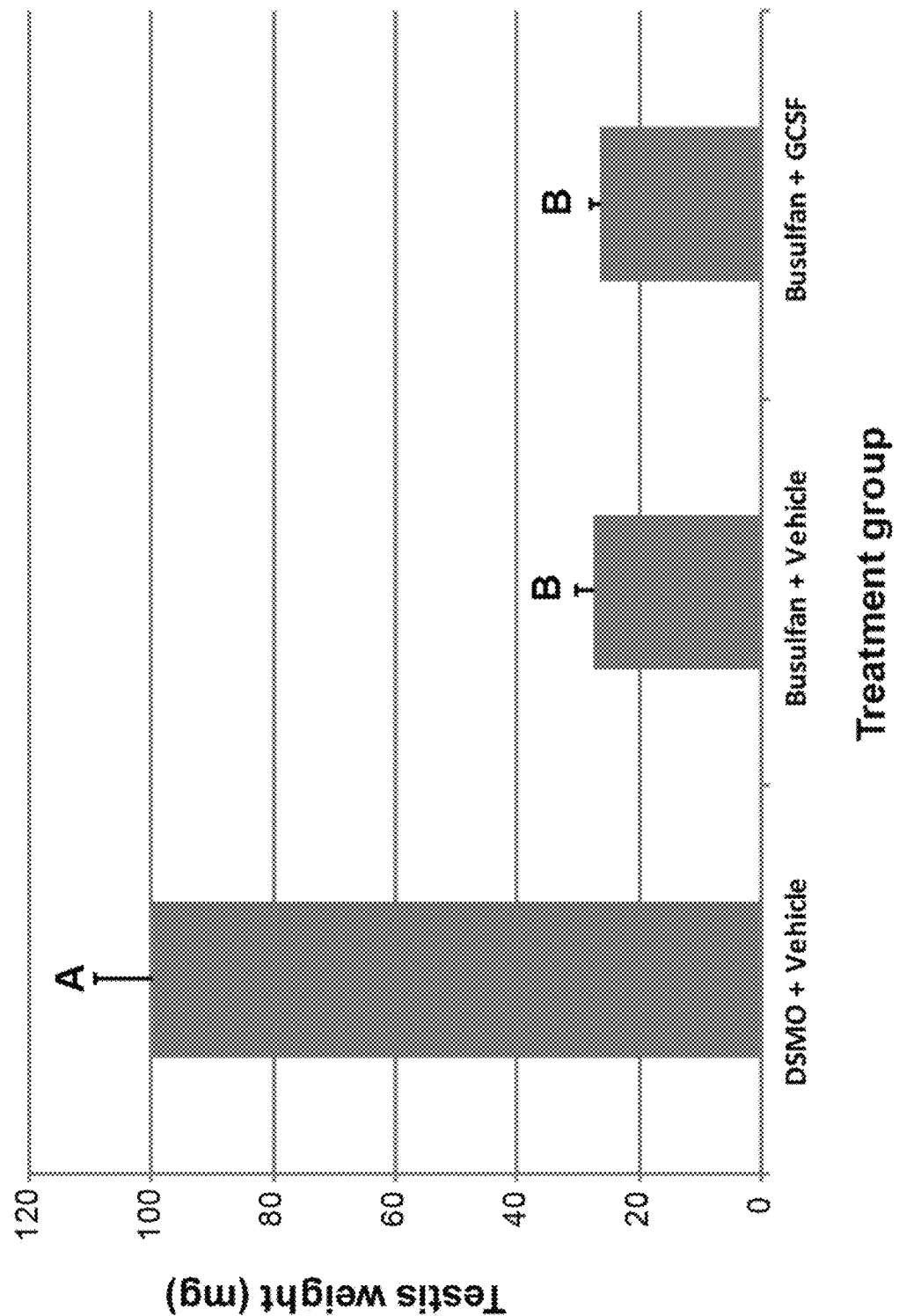
FIG. 4. Mouse testis weights 2 months after busulfan treatment +/−G-CSF. Two months after treatment, testes were removed from the treated mice and weighed. Testes of animals in both groups 2 and 3 (treated with busulfan, noted by 'B') were significantly smaller than controls (noted by 'A'). But, testis weights from animals treated with busulfan+G-CSF were not different from those treated with busulfan+vehicle. Statistical significance was determined by a student's T-test.
Figures 5A, 5B, 5C, 5D, 5E, 5F:
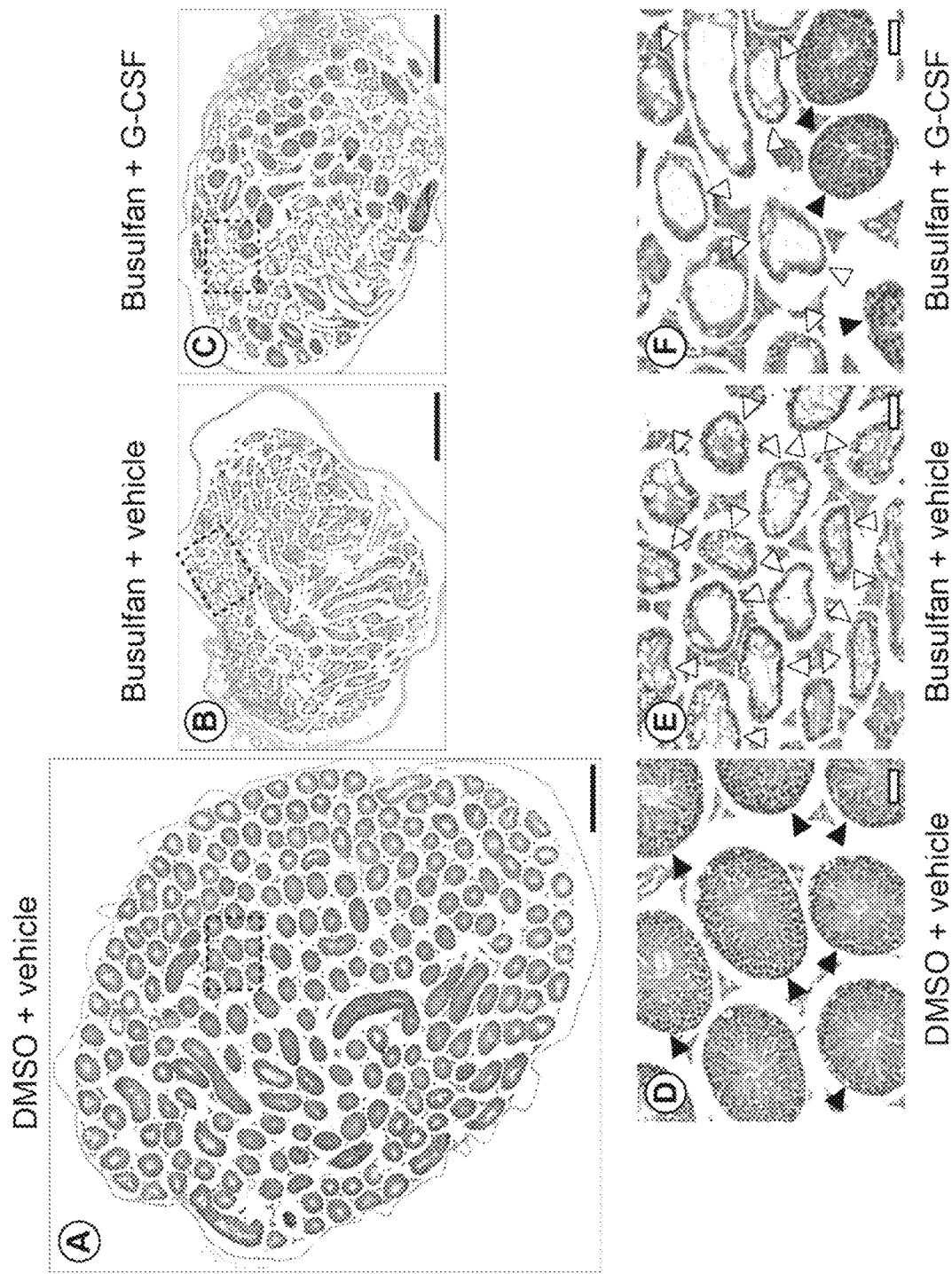
FIGS. 5A-5F. Histological evaluation of mouse testes after busulfan treatment revealed that G-CSF prevents the loss of spermatogenesis. Tiled brightfield images of H&E-stained sections of mouse testes from (A) group 1 (DMSO+vehicle), (B) group 2 (busulfan+vehicle), and (C) group 3 (busulfan+G-CSF). Dashed box inset indicates the area shown in D-F. Scale bars=500 µm. Enlarged images of the dashed boxes in A-C are shown in (D-F), respectively. Scale bars=50 µm. Filled arrowheads=seminiferous tubules with spermatogenesis. Open arrowheads=no spermatogenesis.
Figure 6A:
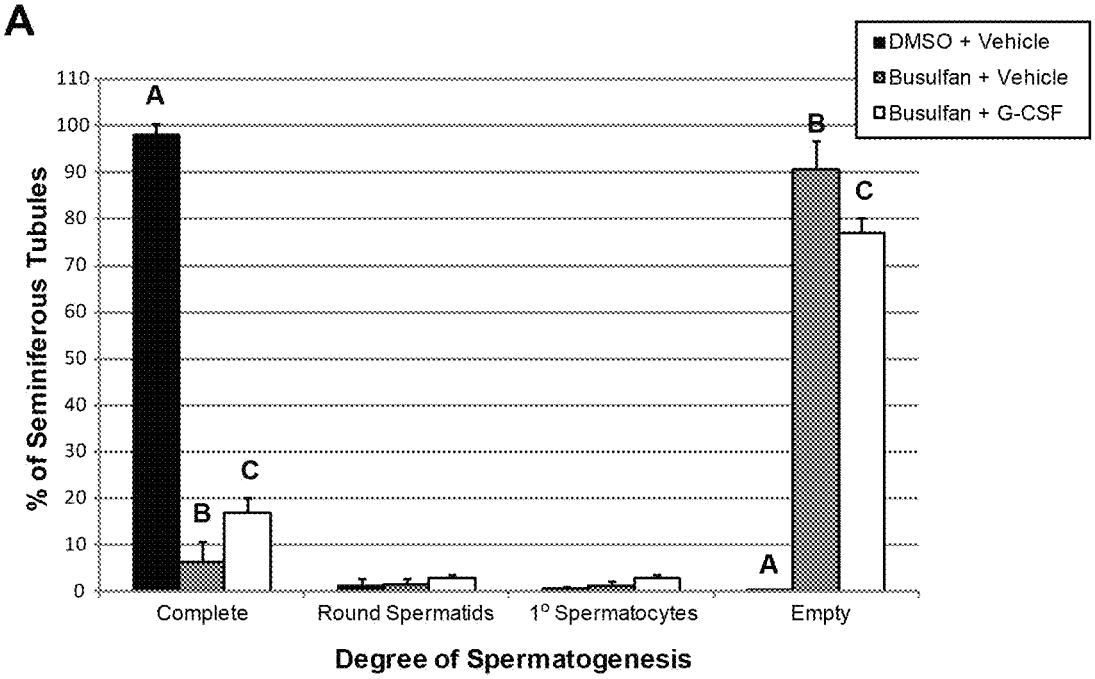
FIGS. 6A-6B. Quantitatively more mouse spermatogenesis was observed after busulfan treatment when mice received G-CSF treatment. Seminiferous tubule cross-sections from mice treated as shown in FIG. 5 were systematically counted and categorized as containing complete spermatogenesis (complete), up to round spermatid stage (round spermatids), up to primary spermatocytes (1° spermatocytes), or containing no spermatogenesis (empty or Sertoli cell-only). (A) The percentage of all seminiferous tubule cross-sections counted from all animals in each group which fall in the four categories is shown. All three groups were significantly different from each other when comparing the percentage of tubules with either complete spermatogenesis or empty (see A, B, and C categorical notations above bars). That is, compared to busulfan treatment alone, mice receiving G-CSF in addition to busulfan had significantly more tubules containing complete spermatogenesis and significantly fewer empty tubules. (B) The same data presented in A are combined by group to show the percentage of seminiferous tubules containing any spermatogenesis or no spermatogenesis (empty bar segment). Again, all three groups were significantly different from each other (see A, B, and C categorical notations above bar segments). That is, G-CSF treatment resulted in significantly more spermatogenesis (at any degree of differentiation) compared with busulfan treatment alone. Statistically significant results ($p<0.05$) were determined by Tukey-Kramer ANOVA.
Figure 6B:
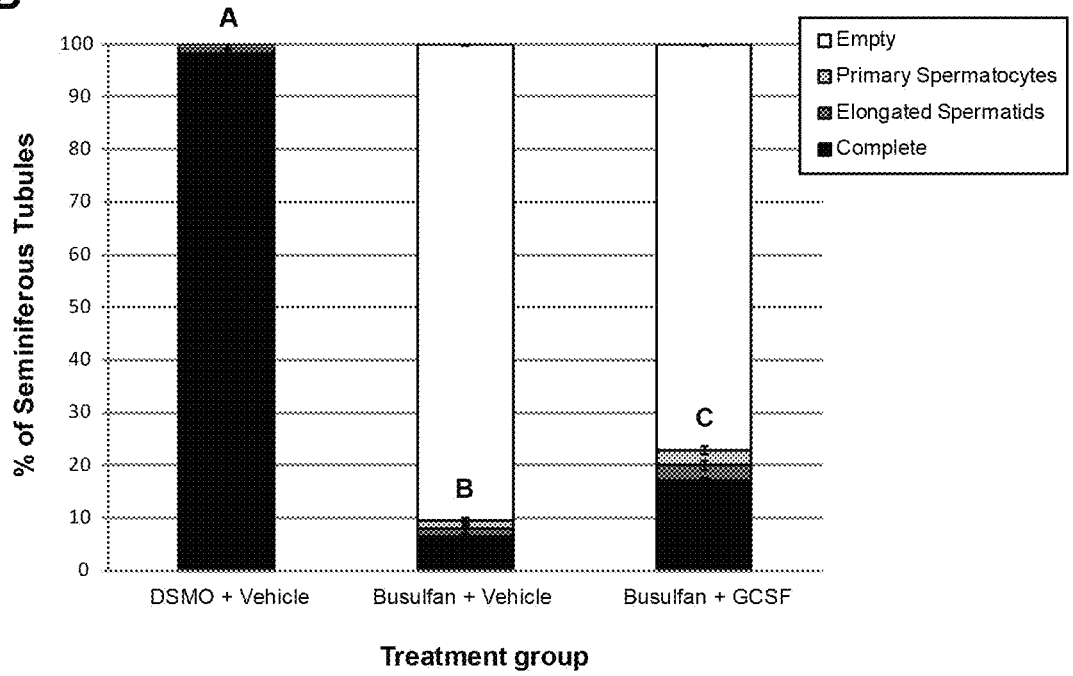

The results of meta-analysis of the rhesus macaque busulfan studies prompted additional studies in mice to (1) replicate the results observed in rhesus macaques and (2)

determine whether G-CSF could act directly upon testicular germ cells to prevent male infertility after busulfan treatment. In the first experiment, 5 week-old C57BL/6 mice were treated with G-CSF for one week (50 µg/kg/day) and administered busulfan (44 mg/kg) on day 3 (see FIG. 3), mimicking the approach used to administer G-CSF in rhesus monkeys. Two months after completing G-CSF treatment, the mice euthanized and their testes removed. Testis weights were significantly reduced in animals treated with busulfan (groups 2 and 3), compared with controls (group 1), but did not differ significantly between animals treated with busulfan +G-CSF or busulfan alone (FIG. 4). The testes were then analyzed histologically (FIG. 5) to determine if G-CSF treatment affected the degree of spermatogenesis after busulfan treatment. Unlike control testes, in which most tubules contained complete spermatogenesis (FIGS. 5A and D), many tubules were devoid of germ cells (empty or Sertoli cell-only) in animals treated with busulfan (FIGS. 5B-C and E-F). However, tubules were observed in animals from both groups 2 and 3 which contained varying degrees of spermatogenesis, and thus, the degree of spermatogenesis was quantified in seminiferous tubule cross sections from each mouse in the study. Histological analysis demonstrated that treatment with G-CSF led to significantly better recovery of spermatogenesis after busulfan treatment than controls (FIG. 6). Animals treated with busulfan alone had significantly less spermatogenesis two months after treatment (compared to control animals; FIG. 6). However, in mice that received 2 day pre-treatment and 5 day post-treatment with G-CSF (50 µg/kg) in addition to busulfan, significantly more seminiferous tubules were observed that contained complete spermatogenesis (FIG. 6A), significantly less empty seminiferous tubules (FIG. 6A), and significantly more tubules with any degree of spermatogenesis (FIG. 6B) than busulfan alone. This suggested that the G-CSF treatments protected SSC and/or spermatogenesis from damage by chemotherapy.

Figure 7A:
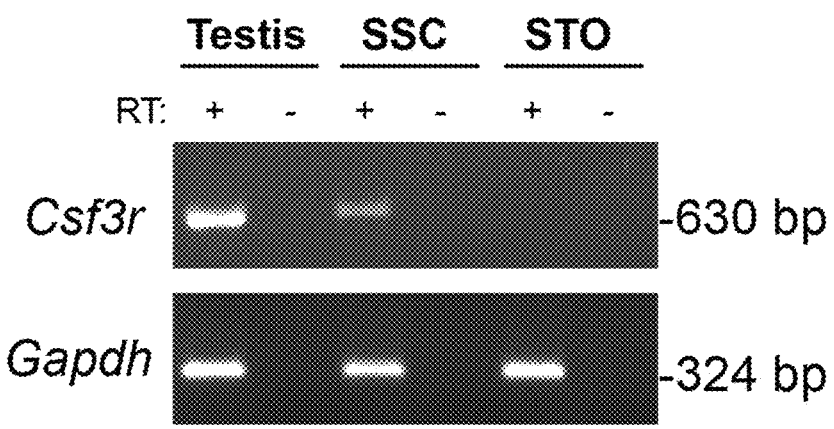
FIGS. 7A-7B. The cell-surface receptor for G-CSF, CSF3R, is present in the testis and on SSCs. Csf3 receptor (Csf3r) mRNA and CSFR3 protein are present in the adult mouse testis and mouse SSC cultures. (A) RT-PCR was performed to detect the mRNAs for (top) Csf3r and (bottom) Gapdh in adult testis, cultured mouse SSCs and SNL76/7 STO feeders (STO) using previously published primers. Csf3r mRNA was detected in both testis, ex vivo SSC cultures, but was absent from STO cells. Template samples generated from RNA with reverse transcriptase (+RT) or without reverse transcriptase (−RT) are shown for each tissue/cell sample. No evidence of genomic DNA contamination was observed in any sample. (B) Western blot was used to detect CSF3R protein in liver (positive control), adult testis and cultured SSCs using sheep anti-mouse CSF3R (R&D systems, AF6039; 1:1000). A prominent band with a molecular weight slightly less than 75 kDa was observed in all three samples and a less-prominent band of slightly more than 100 kDa only in the liver sample. Both molecular weights have been previously reported for CSF3R.
Figure 7B:
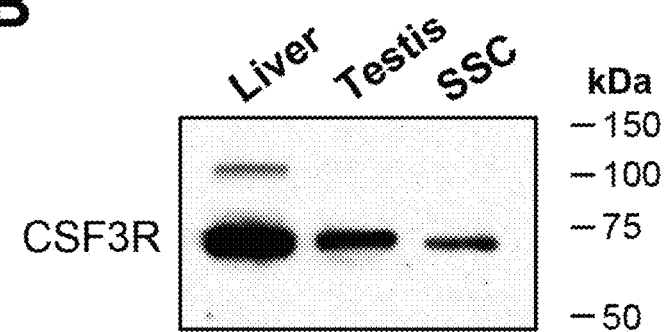
Figures 8A, 8B, 8C, 8D, 8E, 8F:
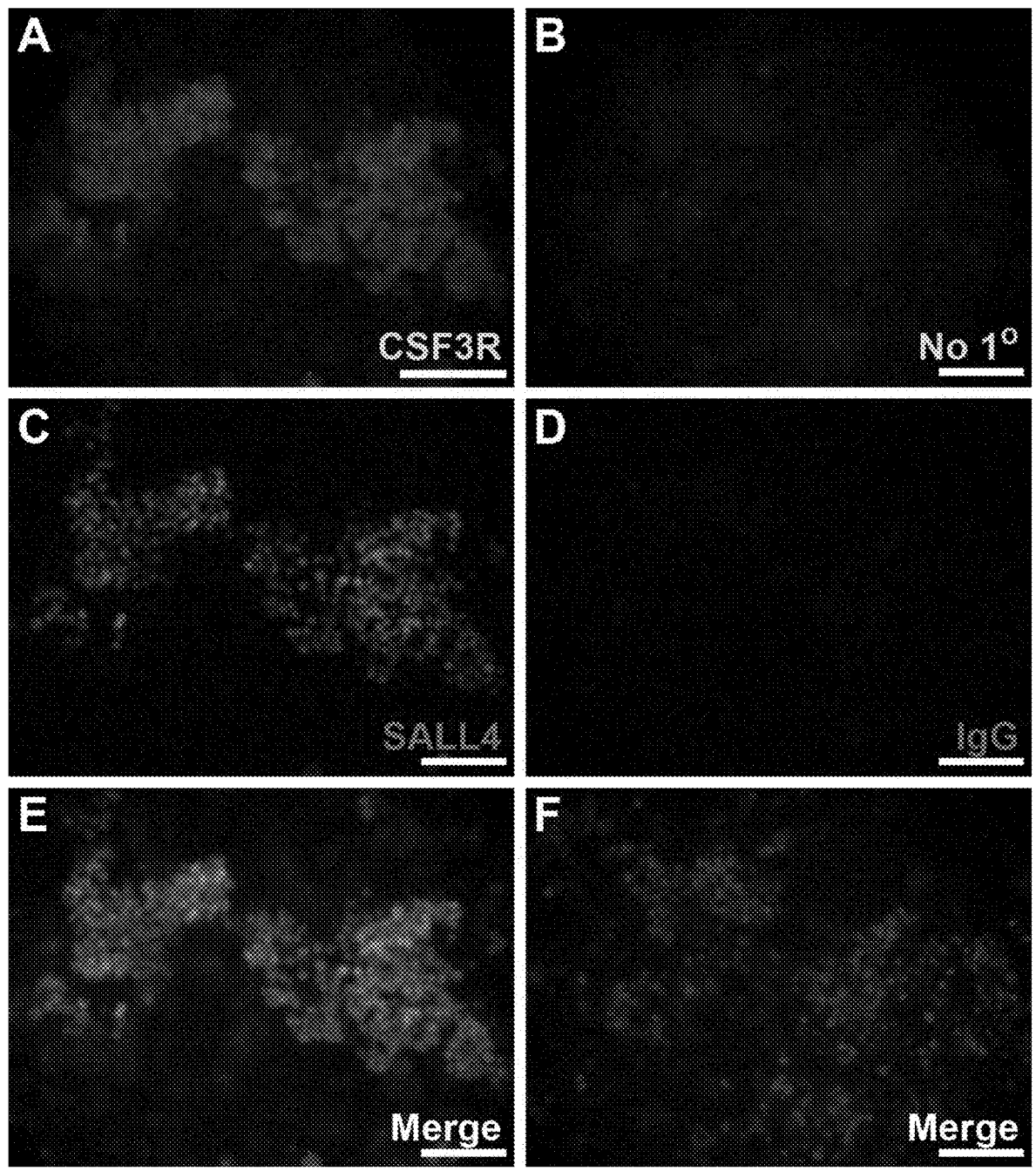
FIGS. 8A-8F. Immunolocalization of CSFR3 protein in cultured mouse SSCs. To confirm that the RT-PCR and Western blot data indicating the G-CSF receptor is present in cultured SSCs, immunofluorescent staining for CSF3R protein was performed in ex vivo mouse SSC cultures using antibodies that recognize (A) CSF3R (R&D Systems, AF6039; 2 µg/ml) and (C) SALL4 (Abcam, Ab29112; 1.6 µg/ml), a marker of undifferentiated spermatogonia (including SSCs) and (E) merged image of both CSF3R and SALL4 together with Hoechst 33342 counterstain (DNA). Staining was compared to (B) omission of 1° antibody, (B) rabbit IgG (1.6 µg/ml), and (F) the merged image with Hoechst counterstain. CSF3R staining is clearly visible in nearly all SALL4+spermatogonia.
Figure 9A:
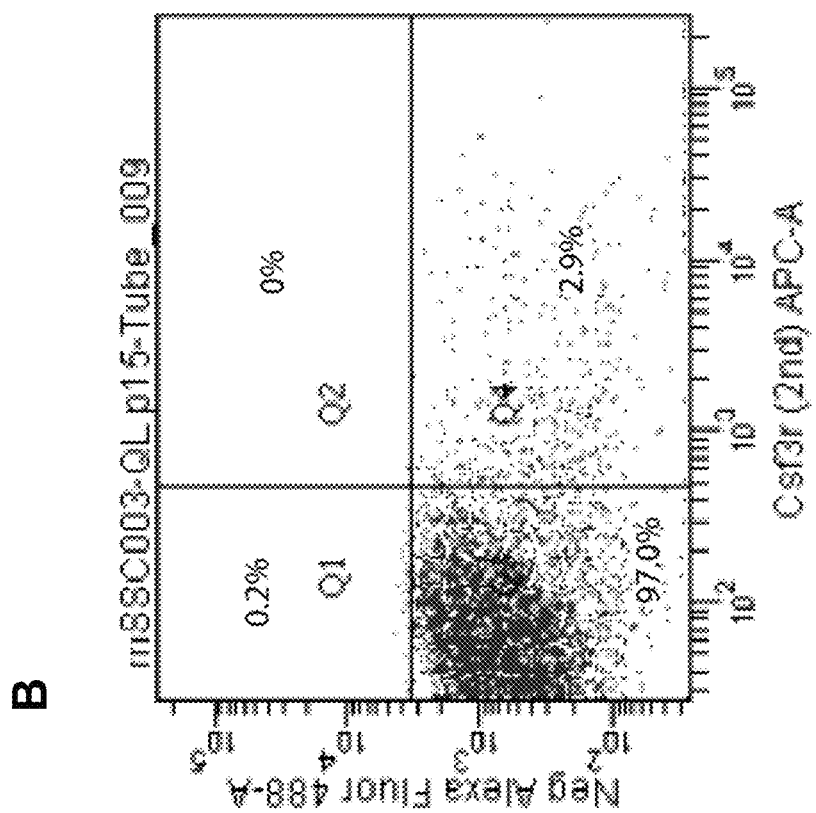
FIGS. 9A-9B. Cell surface detection of CSFR3 protein in cultured mouse SSCs by flow cytometry. To provide further evidence that G-CSF receptor is present on the cell-surface of cultured SSCs, and thus, can potentially respond to G-CSF ligand, flow cytometry was performed by using ex vivo mouse SSC cultures. Live cultured SSCs were stained with (A) isotype control antibodies (mouse IgG2bk; 3 µg/$10^6$) or (B) CSF3R antibodies (Abcam, ab19479; 3 µg/$10^6$). Both samples were stained with goat anti-mouse IgG conjugated with APC. Shown are scatter plots for 25,000 events collected from each sample. Quadrant statistics are shown as percentages in each quadrant. Cell-surface CSF3R staining is clearly visible as dots in quadrant 4 in B (2.9%), compared with only 0.1% of cells in quadrant 4 in the isotype control-stained sample (A).
Figure 9B:
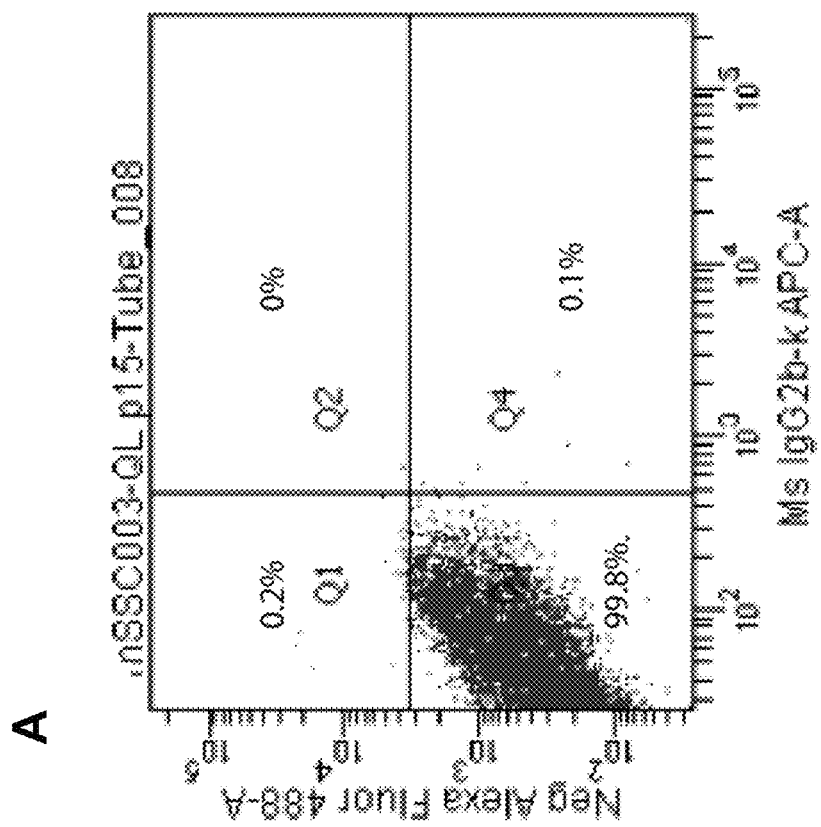

To begin exploring the cellular target of G-CSF in the testis, expression of the receptors for this cytokine (Csf3r) were examined in the mouse male germline (FIG. 7). RNA isolated from adult mouse testis, ex vivo SSC cultures, and SNL 76/7 STO feeder cells (STO) were used for RT-PCR for Csfr3 mRNA. Csf3r mRNA expression was detected in testis and primary mouse SSC cultures, but no detectable expression observed in STO feeder cells (FIG. 7A). Further, expression of CSF3R protein was examined by western blot in testis and SSC protein sample and detected a band corresponding to CSF3R in both samples (FIG. 7B). To confirm that SSCs express CSF3R protein, immunoflourescent co-staining of cultured SSCs for CSF3R and SALL4 was performed (FIG. 8), a marker of undifferentiated spermatogonia, including SSCs. Nearly all of the SALL4+ spermatogonia in our SSC cultures were also labeled for CSF3R (FIG. 8A, C, E), suggesting that SSCs express this protein. Moreover, flow cytometry was employed using cultured SSCs to detect CSF3R on the cell surface of SSCs (FIG. 9). Significantly more SSCs were labeled with antibodies against CSF3R (2.9%, quadrant 4; FIG. 9B) than with isotype control antibodies (0.1%, quadrant 4; FIG. 9A). Thus, G-CSF could be acting directly on the germ cells in the spermatogenic lineage, and more specifically, likely at the level of SSCs.

Figure 10:
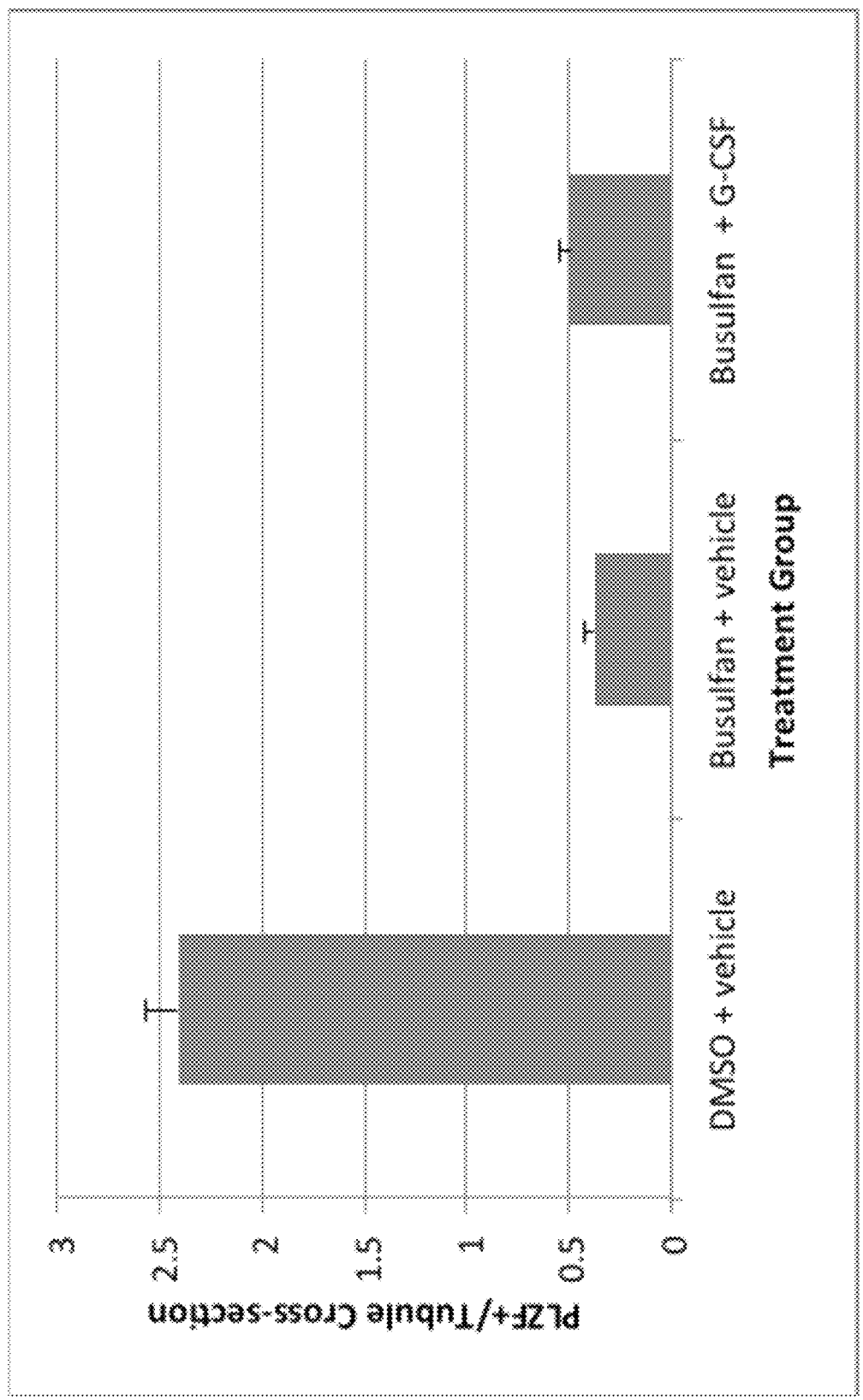
FIG. 10. There are significantly more PLZF+spermatogonia 5 days following busulfan treatment when animals are also treated with G-CSF. The numbers of PLZF+spermatogonia in stained testis sections from mice treated as in FIG. 3 and analyzed as in FIG. 3D are shown. The number of PLZF+spermatogonia per tubule cross-section was significantly higher in animals treated with G-CSF+busulfan compared with busulfan alone (*; p=0.035). The numbers of PLZF+spermatogonia per tubule were significantly lower in both busulfan-treated groups than vehicle-treated animals. Statistical significance was determined by student's T-test.

Five days after busulfan treatment there were significantly more PLZF+ (a transcription factor which is specifically expressed by spermatogonial stem cells and other non-stem undifferentiated spermatogonia in the testis) spermatogonia following busulfan treatment when animals are also treated with G-CSF (FIG. 10). Shown in FIG. 10 are the numbers of PLZF+spermatogonia in stained testis sections from mice treated as in FIG. 3. The number of PLZF+spermatogonia per tubule cross-section was significantly higher in animals treated with G-CSF+busulfan compared with busulfan alone (*; p=0.035). The numbers of PLZF+spermatogonia per tubule were significantly lower in both busulfan-treated groups than vehicle-treated animals. Statistical significance was determined by student's T-test.

Figure 11:
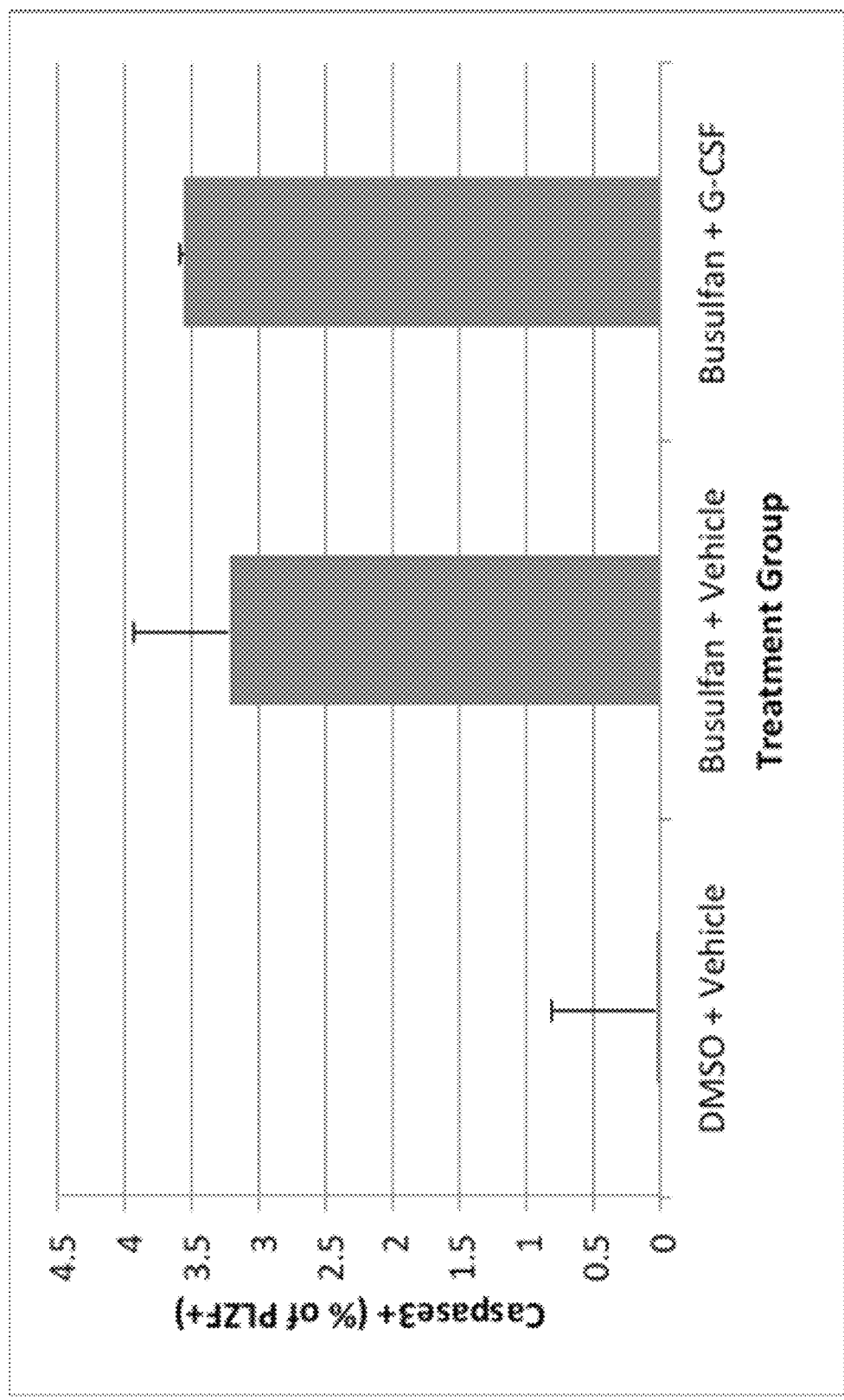
FIG. 11. G-CSF treatment does not reduce the proportion of PLZF+spermatogonia undergoing early apoptosis 5 days after Busulfan treatment. Despite increased numbers of PLZF+spermatogonia in busulfan-treated animals that also received G-CSF (FIG. 10), the proportions of PLZF+spermatogonia that were positive for activated Caspase 3 (top) were not different between animals treated with G-CSF compared to busulfan alone (p=0.38).
Figure 12:
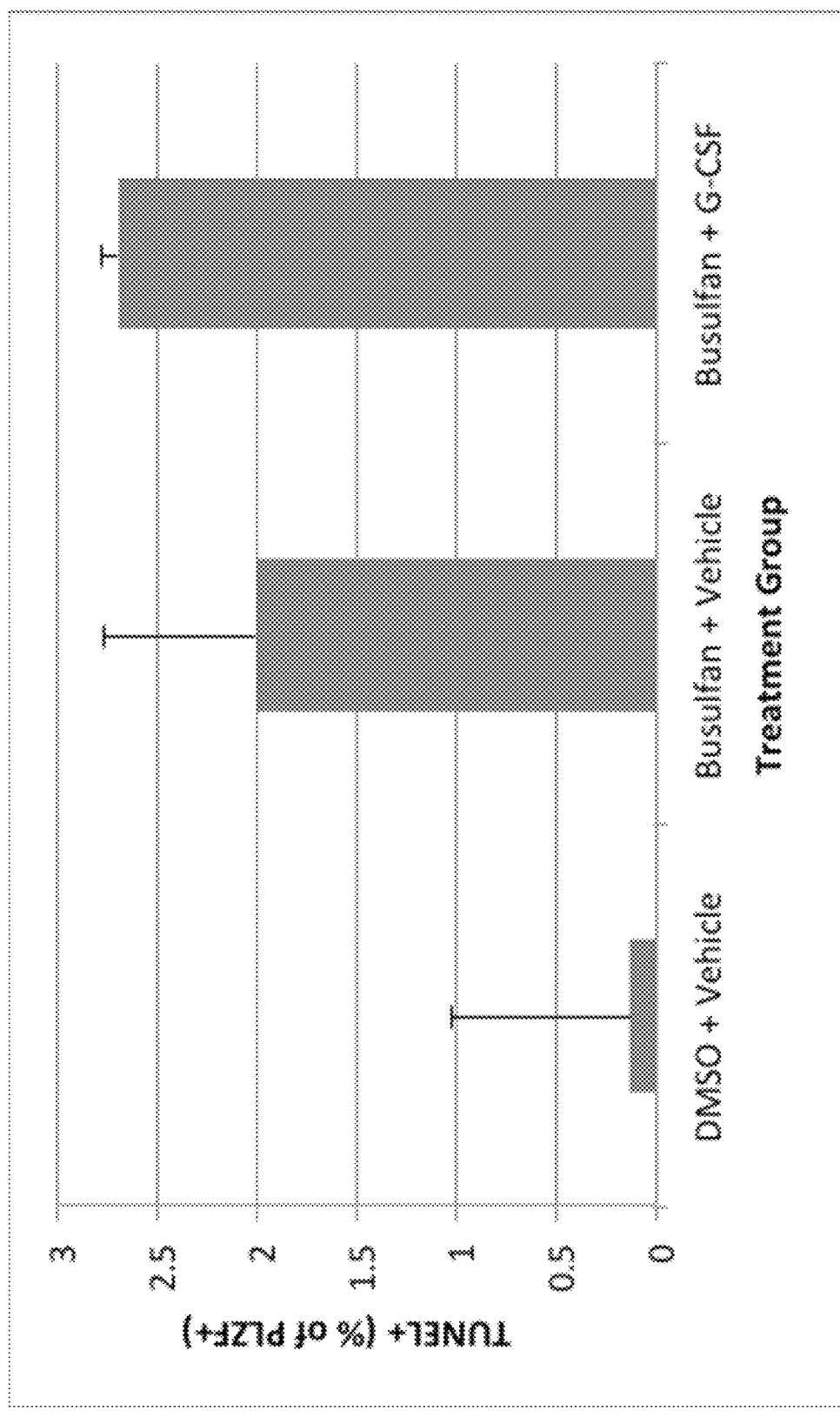
FIG. 12. G-CSF treatment does not reduce the proportion of PLZF+spermatogonia undergoing late apoptosis 5 days after Busulfan treatment. Despite increased numbers of PLZF+spermatogonia in busulfan-treated animals that also received G-CSF (FIG. 10), the proportions of PLZF+spermatogonia that were positive for TUNEL were not different between animals treated with G-CSF compared to busulfan alone (p=0.28).

At five days post-busulfan treatment, it was found that G-CSF treatment does not reduce the proportion of PLZF+ spermatogonia undergoing apoptosis. Despite increased numbers of PLZF+spermatogonia in busulfan-treated animals that also received G-CSF, the proportions of PLZF+ spermatogonia that were positive for activated Caspase 3 (FIG. 11) or TUNEL (FIG. 12) were not different between animals treated with G-CSF compared to busulfan alone (p=0.38 and p=0.28, respectively).

It is suspected that G-CSF may prevent the damaging effects of chemotherapy on spermatogenesis and male fertility by promoting proliferation of SSCs after chemotherapy (i.e., promote regeneration of spermatogenesis). Since G-CSF is known to be a mitogen in the hematopoietic system, this is a possible mechanism by which G-CSF abrogates chemotherapy damage on spermatogenesis by simply causing greater proliferation of SSCs and/or other germ cells of the testis after chemotherapy. However, G-CSF is also known to prevent apoptosis in neutrophil precursors and motor neurons, and thus, it may have similar effects on SSCs and/or other germ cells in the testis. In this case, SSCs would be protected from the toxic effects of chemotherapy by the anti-apoptotic influences of G-CSF.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A method of ameliorating chemotherapy-induced infertility comprising:
    administering an effective amount of granulocyte colony-stimulating factor (GCSF) to a human male subject 1 to 7 days prior to and after administration of an alkylating chemotherapeutic agent,
    wherein chemotherapy-induced infertility is ameliorated.

2. The method of claim 1, wherein the alkylating chemotherapeutic agent is busulfan.

3. The method of claim 1, wherein the effective amount of granulocyte colony-stimulating factor is from about 0.1 µg/kg/day to about 500 µg/kg/day.

* * * * *